(12) United States Patent
Shih et al.

(10) Patent No.: US 11,957,444 B2
(45) Date of Patent: Apr. 16, 2024

(54) METHODS AND SYSTEMS FOR FUNCTIONAL MAGNETIC RESONANCE IMAGING WITH A ZERO ECHO TIME PULSE-SEQUENCE

(71) Applicant: The University of North Carolina at Chapel Hill, Chapel Hill, NC (US)

(72) Inventors: Yen-Yu Shih, Cary, NC (US); Martin John MacKinnon, Raleigh, NC (US); Yuncong Ma, Chapel Hill, NC (US); Wei-Tang Chang, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 17/882,965

(22) Filed: Aug. 8, 2022

(65) Prior Publication Data
US 2023/0042314 A1    Feb. 9, 2023

Related U.S. Application Data

(60) Provisional application No. 63/230,497, filed on Aug. 6, 2021.

(51) Int. Cl.
*G01R 33/48* (2006.01)
*A61B 5/055* (2006.01)

(52) U.S. Cl.
CPC .............. *A61B 5/055* (2013.01); *G01R 33/48* (2013.01); *G01R 33/4824* (2013.01)

(58) Field of Classification Search
CPC . A61B 5/055; A61B 2576/026; A61B 5/0042; A61B 5/14542; G01R 33/48; G01R 33/4824; G01R 33/4826; G01R 33/4816; G01R 33/4806
See application file for complete search history.

(56) References Cited

U.S. PATENT DOCUMENTS

2020/0191892 A1*    6/2020    Corum ............. G01R 33/56341

OTHER PUBLICATIONS

Ljungberg et al. Silent zero TE MR neuroimaging: Current state-of-the-art and future directions, Progress in Nuclear Mag. Reson. Spectroscopy, 123 (2021) 73-93. (Year: 2021).*

(Continued)

*Primary Examiner* — G. M. A Hyder
(74) *Attorney, Agent, or Firm* — Jenkins, Taylor & Hunt, P.A.

(57) ABSTRACT

This specification describes systems and methods for using Zero Echo Time (ZTE) magnetic resonance imaging (MRI) sequences for applications to functional MRI (fMRI). In some examples, a system for functional magnetic resonance imaging includes a magnetic resonance imaging (MRI) scanner and a control console implemented on at least one processor. The control console is configured for executing, using the MRI scanner, a zero echo time (ZTE) pulse sequence; acquiring, using the MRI scanner, magnetic resonance data in response to the ZTE pulse sequence; and constructing at least one MRI image using the magnetic resonance data and measuring tissue oxygenation (PtO2)-related T1 changes as a proxy of neural activity changes of a subject using the at least one MRI image.

19 Claims, 12 Drawing Sheets

(56) References Cited

OTHER PUBLICATIONS

Mackinnon, M. J. et al. i-ZTE fMRI (https://www.ismrm.org/20/program_files/O77.htm). in International Society for Magnetic Resonance in Medicine (2020).

Smitha, et al., "Resting state fMRI: A review on methods in resting state connectivity analysis and resting state networks", Neuroradiology Journal (2017). doi:10.1177/1971400917697342.

Welberg, L. Neuroimaging: Rats join the 'default mode' club. Nat. Rev. Neurosci. (2012). doi:10.1038/nrn3224.

Mandeville, J. B. et al. Dynamic functional imaging of relative cerebral blood volume during rat forepaw stimulation. Magn. Reson. Med. (1998). doi: 10.1002/mrm.1910390415.

Kim, et al., "Cerebral blood vol. MRI with intravascular superparamagnetic iron oxide nanoparticles", NMR Biomed. (2013). doi: 10.1002/nbm.2885.

Shih, et al., "Striatal and cortical BOLD, blood flow, blood vol. oxygen consumption, and glucose consumption changes in noxious forepaw electrical stimulation", J. Cereb. Blood Flow Metab. (2011). doi:10.1038/jcbfm.2010.173.

Shih, et al., "Endogenous opioid-dopamine neurotransmission underlie negative CBV fMRI signals", Exp. Neurol. (2012). doi:10.1016/j.expneurol.2011.12.042.

Chen, et al., "Dopaminergic imaging of nonmotor manifestations in a rat model of Parkinson's disease by fMRI", Neurobiol. Dis. (2013). doi:10.1016/j.nbd.2012.07.020.

Ryali, et al., "Combining optogenetic stimulation and fMRI to validate a multivariate dynamical systems model for estimating causal brain interactions", (https://www.pathlms.com/ohbm/courses/5158/video_presentations/78854). in The Organization for Human Brain Mapping (2017).

Shih, et al., "Imaging neurovascular function and functional recovery after stroke in the rat striatum using forepaw stimulation", J. Cereb. Blood Flow Metab., pp. 1483-1492 (2014). doi:10.1038/jcbfm.2014.103.

Lai, et al., "Functional MRI reveals frequency-dependent responses during deep brain stimulation at the subthalamic nucleus or internal globus pallidus", Neuroimage (2013). doi:10.1016/j.neuroimage.2013.08.026.

Lai, et al., "Robust deep brain stimulation functional MRI procedures in rats and mice using an MR-compatible tungsten microwire electrode", Magn. Reson. Med. (2015). doi:10.1002/mrm.25239.

Van Den Berge, et al., "Functional circuit mapping of striatal output nuclei using simultaneous deep brain stimulation and fMRI", Neuroimage, pp. 1-21 (2017). doi:10.1016/j.neuroimage.2016.10.049.

Shih, et al., "A new scenario for negative functional magnetic resonance imaging signals: Endogenous neurotransmission", J. Neurosci., vol. 29(10), pp. 3036-3044 (2009). doi:10.1523/JNEUROSCI.3447-08.2009.

Shih, et al., "Ultra high-resolution fMRI and electrophysiology of the rat primary somatosensory cortex", Neuroimage, pp. 113-120 (2013).

* cited by examiner

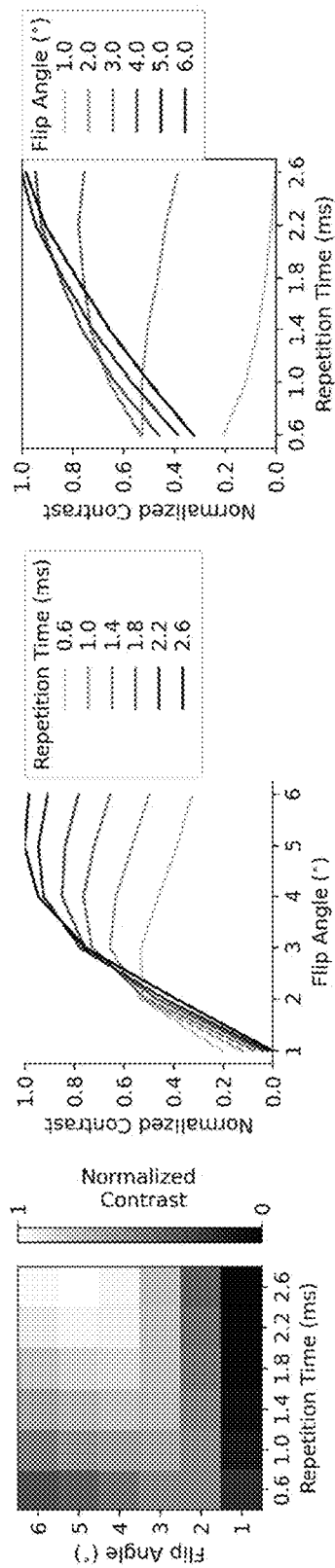
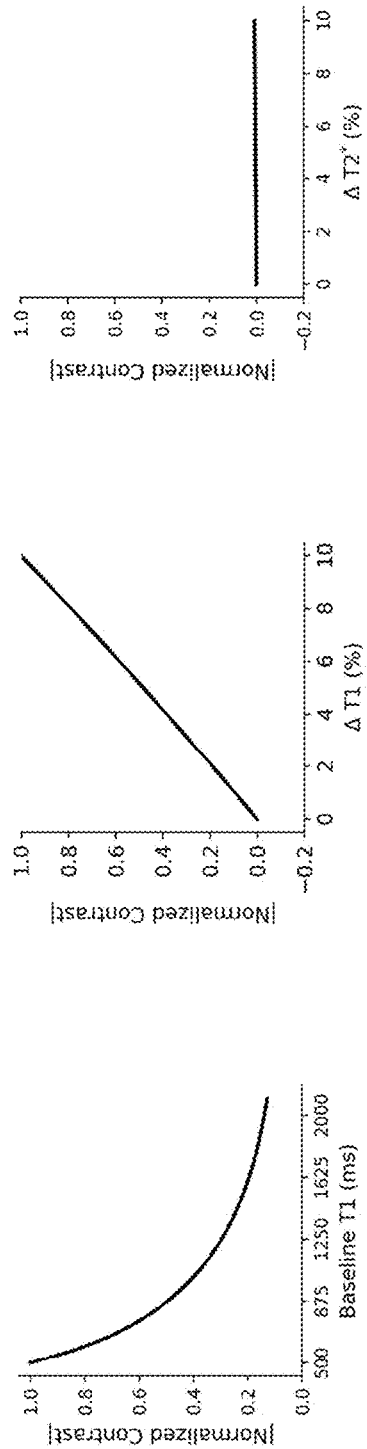
FIG. 4A
FIG. 4B
FIG. 4C
FIG. 4D

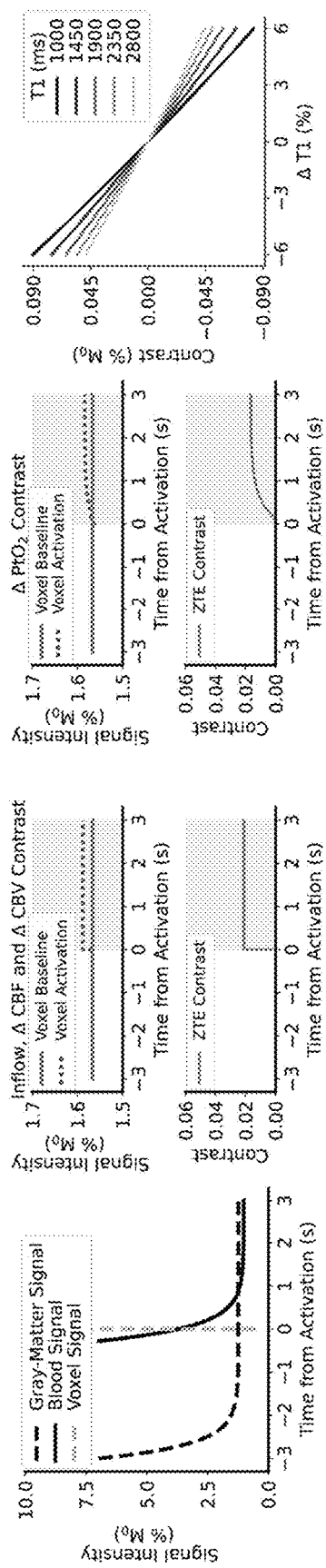

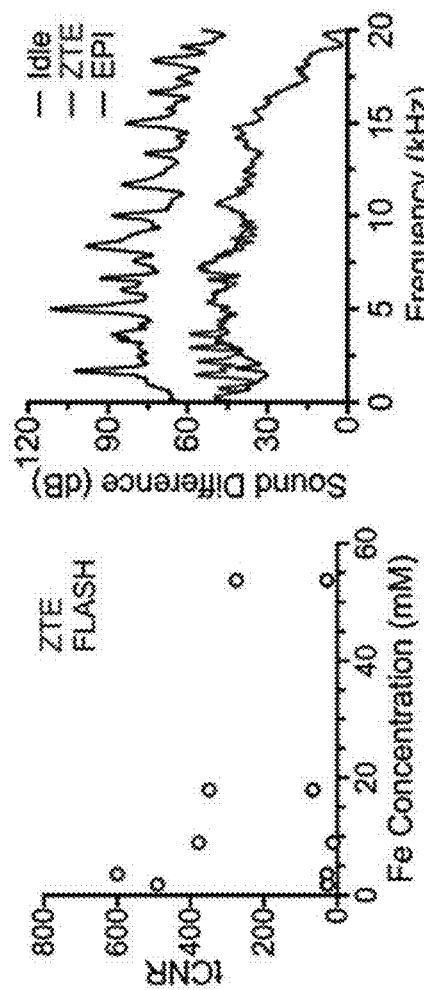
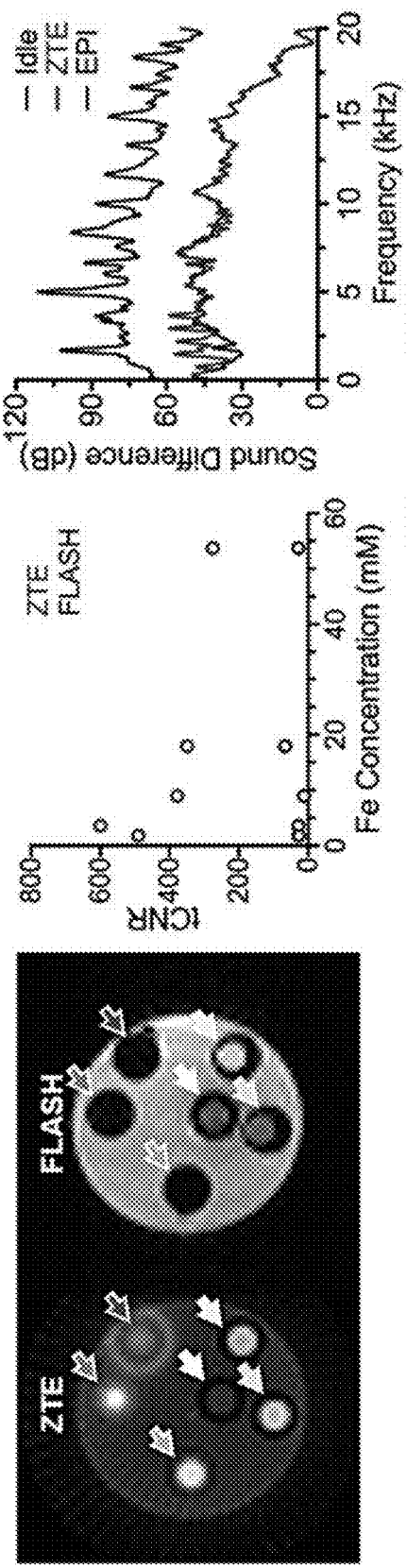
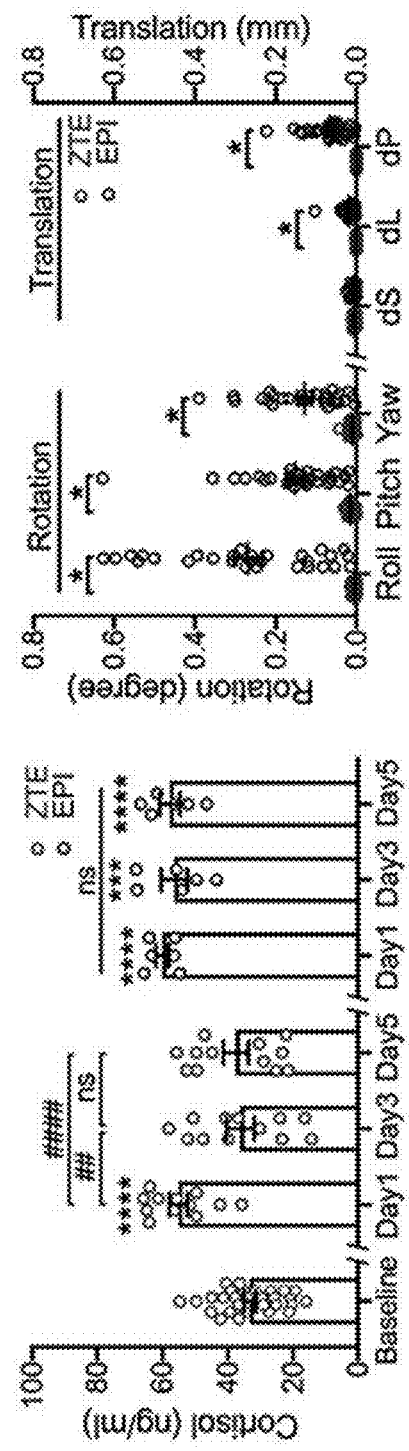
FIG. 13A  FIG. 13B  FIG. 13C  FIG. 13D  FIG. 13E

METHODS AND SYSTEMS FOR FUNCTIONAL MAGNETIC RESONANCE IMAGING WITH A ZERO ECHO TIME PULSE-SEQUENCE

PRIORITY CLAIM

This application claims the benefit of U.S. Provisional Patent Application Ser. No. 63/230,497 filed Aug. 6, 2021, the disclosure of which is incorporated herein by reference in its entirety.

STATEMENT OF GOVERNMENT INTEREST

This invention was made with government support under grant numbers MH111429 and MH126518 awarded by the National Institutes of Health. The government has certain rights in the invention.

TECHNICAL FIELD

This specification relates generally to using low-bandwidth Zero Echo Time (ZTE) magnetic resonance imaging (MRI) sequences for applications to functional MRI (fMRI).

BACKGROUND

MRI is a non-ionizing and non-invasive imaging modality, used for a variety of anatomical and functional techniques. Conventional MRI involves the excitation of the hydrogen protons (hereafter termed spins) that are precessing in a strong magnetic field following a radiofrequency (RF) pulse. RF pulse excitation flips the net magnetization vector from the longitudinal direction towards the transverse plane, creating the MR signal. The transverse component of magnetization decays due to $T2/T2^*$ relaxation. The longitudinal component of magnetization restores back to the thermal equilibrium due to T1 relaxation. In the time between successive RF pulses, the MRI signal is spatially encoded by the gradient magnetic fields which are conventionally switched on and off between every RF pulse repetition.

Over the past three decades, Gradient Recalled Echo (GRE)-Echo Planar Imaging (EPI)-based Blood Oxygen Level Dependent (BOLD) functional magnetic resonance imaging (fMRI) has become established as the most-widely-used non-invasive functional neuroimaging technique. GRE-EPI benefits from strong magnetic fields to achieve optimal sensitivity, but it has several major undesirable properties.

a) Sensitivity to magnetic field inhomogeneity artifacts. A consequence of the "blipped" spatial encoding trajectory and low bandwidth in the phase encoding direction of GRE-EPI is profound artifacts, predominantly owing to magnetic susceptibility gradients and motion.

b) High acoustic noise. MRI scanning is often associated with intense acoustic noise, a result of vibration of the gradient coils when driven by electrical current. GRE-EPI generates particularly severe acoustic noise, due to the high gradient-power duty cycle of the sequence and the need to rapidly switch gradient polarity during spatial encoding. In human fMRI studies; experiments including pediatric subjects may be particularly compromised, as well as those investigating resting-state functional connectivity and the auditory system. In preclinical studies, fMRI experiments conducted with awake animals are potentially biased by increased stress, motion and altered behavior.

c) Poor spatial specificity to the site of neuronal activation. The functional contrast of GRE-EPI fMRI studies is weighted towards areas of dense venous vasculature. Techniques more localized to capillaries than veins are said to be more specific since the location of functional activation is closer to the site of neuronal activation. Thus, the interpretation of GRE-EPI fMRI data is hindered by its spatial non-specificity and requires anatomical knowledge of the underlying vasculature at locations of functional activation and often post-processing techniques to remove the contribution of large venous vasculature.

d) Poor sensitivity. Despite the advent of a variety of fMRI techniques, none has surpassed the sensitivity of GRE-EPI. An fMRI technique with greater sensitivity than the currently most widely used technique would allow the spatial and temporal resolution of fMRI to be increased more efficiently than GRE-EPI.

Alternative fMRI techniques have been developed to address some of the problems of GRE-EPI. However, techniques that Improve the spatial specificity of functional activations suffer from either significantly reduced sensitivity or longer data acquisition time. The most commonly used method to increase the sensitivity beyond conventional GRE-EPI BOLD fMRI requires invasive injection of magnetic contrast agents. It is therefore desirable to develop a method that addresses all of the aforementioned limitations of conventional fMRI.

SUMMARY

This specification describes systems and methods for using Zero Echo Time (ZTE) magnetic resonance imaging (MRI) sequences for applications to functional MRI (fMRI). In some examples, a system for functional magnetic resonance imaging includes a magnetic resonance imaging (MRI) scanner and a control console implemented on at least one processor. The control console is configured for executing, using the MRI scanner, a zero echo time (ZTE) pulse sequence; acquiring, using the MRI scanner, magnetic resonance data in response to the ZTE pulse sequence; and constructing at least one MRI image using the magnetic resonance data and measuring inflow and T1 changes as a proxy of neural activity changes of a subject using the at least one MRI image.

The computer systems described in this specification may be implemented in hardware, software, firmware, or combinations of hardware, software and/or firmware. In some examples, the computer systems described in this specification may be Implemented using a non-transitory computer readable medium storing computer executable instructions that when executed by one or more processors of a computer cause the computer to perform operations. Computer readable media suitable for implementing the subject matter described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application specific integrated circuits. In addition, a computer readable medium that implements the subject matter described in this specification may be located on a single device or computing platform, may be distributed across multiple devices or computing platforms, or may use cloud-based storage and/or processing.

BRIEF DESCRIPTION OF DRAWINGS

FIG. 4A shows the achievable functional contrast for various TRs and flip angles.

FIG. 4B shows that the contrast of ZTE-fMRI can be increased at lower physiological baseline T1 values.

FIG. 4C demonstrates the relationship between percentage T1 change and maximum contrast, within the range of realistic ZTE-fMRI imaging parameters.

FIG. 4D demonstrates that the contrast of ZTE-fMRI is minimally affected by T2* changes.

FIGS. 5A-5D illustrate the relative contributions of tissue T1, blood T1, inflow (CBF & CBV) and $PtO_2$ to ZTE-fMRI contrast in the mouse brain at 9.4T.

FIGS. 13A-13F show that the ZTE-fMRI sequence provides several promising features at 9.4T.

DESCRIPTION

This specification describes systems and methods for using Zero Echo Time (ZTE) magnetic resonance imaging (MRI) sequences for applications to functional MRI (fMRI).

An MRI sequence framework that can address the limitations of some conventional systems is that of a ZTE pulse sequence. So-called ZTE sequences confer numerous benefits that address the described limitations of GRE-EPI BOLD fMRI. Owing to their short acquisition delay, ZTE sequences were developed for the primary application of imaging short T2* species, that are "invisible" with conventional MRI. Primary applications for ZTE sequences to-date include, but are not limited to, imaging of short T2* components in the musculoskeletal system as well as bone and myelin. This document presents a new fMRI application for the ZTE pulse sequence. With modifications to the general ZTE pulse sequence framework and careful modeling of pulse sequence parameters and physiological variables, the methods and systems described in this document demonstrate a new fMRI technique sensitive to tissue oxygenation while overcoming the aforementioned drawbacks of GRE-EPI. This specification is demonstrated in rodents at a magnetic field strength of 9.4 T; however the technique is applicable to humans and across a range of magnetic field strengths.

Figure 1A:
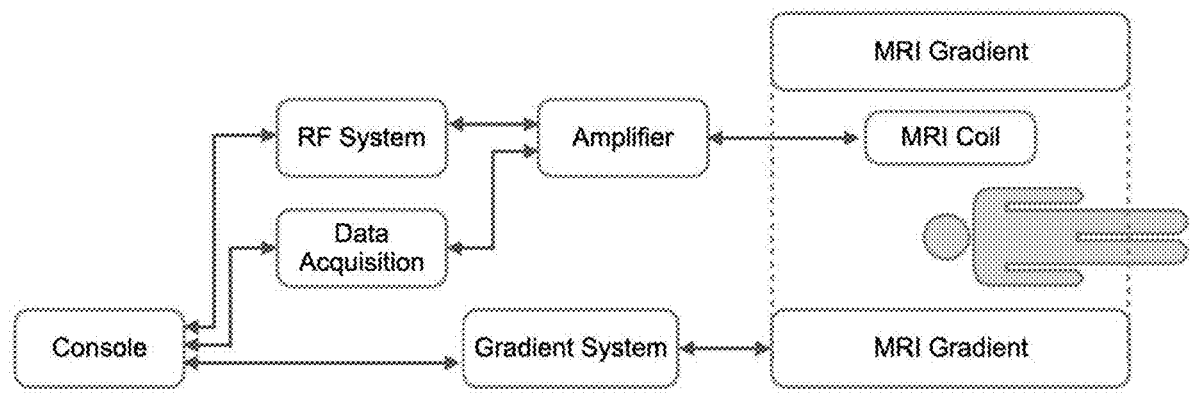
FIG. 1A shows the system for ZTE-fMRI, including a console computer used to set up the sequence parameters and give control to a gradient console and an amplifier to run the sequence.

(1) Imaging System: The system for ZTE-fMRI is shown in FIG. 1A console computer is used to set up the sequence parameters and give control to a gradient console and an amplifier to run the sequence. RF pulses are delivered to the desired region of the subject through the MRI coil(s). Then the signal is received, digitized and stored on the console computer through the same or dedicated receive-only MRI coil(s).

Figures 2A, 2B:
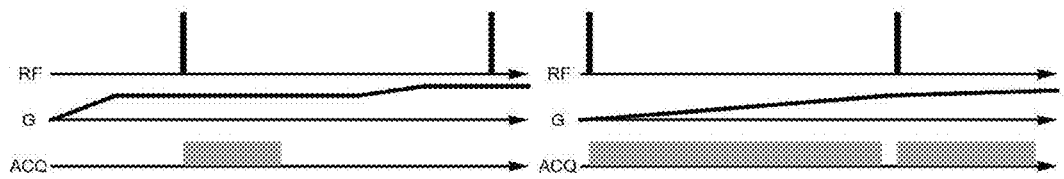
FIG. 2A-2B presents the general framework for two different implementations of the ZTE pulse sequence.

(2) ZTE backbone: The general framework for a ZTE pulse sequence is as presented in FIG. 2A-2B. ZTE employs a spatially non-selective short RF pulse that is applied after the spatial encoding gradients have been applied, in contrast to conventional MRI sequences wherein the spatial encoding gradients are switched on after excitation of magnetization. This affords a short acquisition delay on the order of microseconds, thus conventional ZTE is limited to low flip angles. The repetition time (TR) governs the time between acquisition of successive radial spokes, and one RF pulse is applied per TR. In one implementation strategy, a delay incorporating the gradient ramp time and for the settling of Eddy currents, is set before the application of subsequent RF pulses (FIG. 2A). Alternatively, the gradient can be set to ramp throughout the acquisition negating gradient ramp time and Eddy current settling delays (FIG. 2B). Sampling of radial spokes begins at the center of k-space and moves towards the periphery as the data acquisition progresses. The radial spokes are ordered to cover a sphere in k-space.

(3) Advantages of ZTE-fMRI:

a) Insensitivity to magnetic field inhomogeneities. The short acquisition delay of ZTE renders the sequence insensitive to magnetic field inhomogeneity artifacts including motion, spatial mislocalization and signal dropout as phase accrual of spins is minimized. The radial sampling trajectory of ZTE confers further insensitivity to magnetic field inhomogeneity, due to a variety of rather than two distinct encoding angles, artifacts are reduced by having many encoding directions.

b) Low Acoustic Noise. The gradient encoding trajectory of ZTE Is designed such that the incrementation of gradients between spatial encoding of successive radial spokes is significantly smaller than the gradient strength, resulting in negligible acoustic noise.

c) Improved spatial specificity to the site of neuronal activation. A hallmark of the methods and systems described in this document, following optimization of imaging parameters, is the sensitivity of ZTE to T1 changes. A potential physiological T1-modulater is $PtO_2$. Functionally induced $PtO_2$ changes are localized to the microvasculature, while the BOLD signal is weighted towards the dense venous vasculature. As the microvasculature are closer to neurons, a hallmark of ZTE-fMRI is its improved spatial specificity to neuronal activations. The sensitivity of ZTE-fMRI to functional activations is not limited to $PtO_2$-related changes but any neural activity-related T1 modulators.

d) Higher Sensitivity. Following optimization of imaging parameters for T1 changes as well as substantial reduction or elimination of gradient ramp and Eddy current settling times between spokes, ZTE-fMRI Is more sensitive to functional activations than the gold-standard GRE-EPI.

Figure 1B:
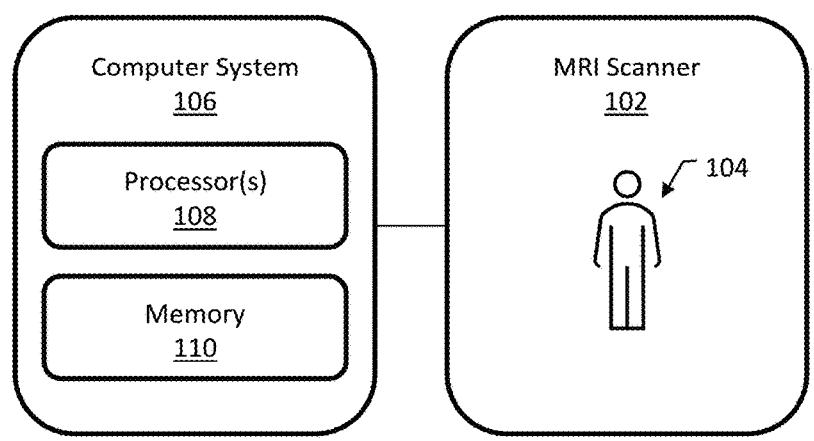
FIG. 1B is a block diagram of an example system for functional magnetic resonance imaging.

FIG. 1B is a block diagram of an example system 100 for functional magnetic resonance imaging. The system 100 includes an MRI scanner 102 configured for imaging a subject 104. The system 100 includes a computer system 106, for example, a control console or a remote cloud computing system communicating with the MRI scanner 102 via a data communications network. The computer system 106 includes at least one processor 108 and memory 110 storing executable instructions for the processor 108.

The computer system 106 is configured for executing, using the MRI scanner 102, a zero echo time (ZTE) pulse sequence. The computer system 106 is configured for acquiring, using the MRI scanner 102, magnetic resonance data in response to the ZTE pulse sequence. The computer system 106 is configured for constructing at least one MRI image using the magnetic resonance data and measuring tissue oxygenation (PtO2)-related T1 changes as a proxy of neural activity changes of a subject using the at least one MRI Image. The computer system 106 can, for example, display the MRI image on a display device or send the MRI image to a remote system for storage or display.

In some examples, executing the ZTE pulse sequence includes applying a spatially non-selective radio frequency pulse after one or more spatial encoding gradients have reached a plateau, and executing the ZTE pulse sequence includes setting a delay before the application of subsequent radio frequency pulses. The delay is based on a gradient ramp time and a settling time for Eddy currents.

In some examples, executing the ZTE pulse sequence Includes applying a spatially non-selective radio frequency pulse while one or more spatial encoding gradients are ramping.

In some examples, executing the ZTE pulse sequence includes adjusting one or more ZTE imaging parameters for sensitivity to T1 changes. Adjusting one or more ZTE imaging parameters for sensitivity to T1 changes can include modifying TR and flip angle to target T1 changes following neuronal functional activation/deactivation. Adjusting one or more ZTE imaging parameters for sensitivity to T1 changes can include optimizing imaging parameters through Bloch equation simulations.

Executing the ZTE pulse sequence can include minimizing ZTE acquisition bandwidth to augment sensitivity or increasing bandwidth to reduce artifacts including magnetic field inhomogeneity-related artifacts. Executing the ZTE pulse sequence can include minimizing the ramp time of a ZTE spatial encoding gradient at a beginning of image acquisition and between each successive spokes of k-space. Executing the ZTE pulse sequence can include ramping the spatial encoding gradients during acquisition. Executing the ZTE pulse sequence can include incorporating RF-spoiling wherein the phase of a RF pulse is varied from each spoke of a plurality of spokes.

In some examples, executing the ZTE pulse sequence comprises integrating an inner shell with short radial spokes and an outer shell with long radial spokes. Executing the ZTE pulse sequence can include using two inverse spiral gradient trajectories.

Figure 6:
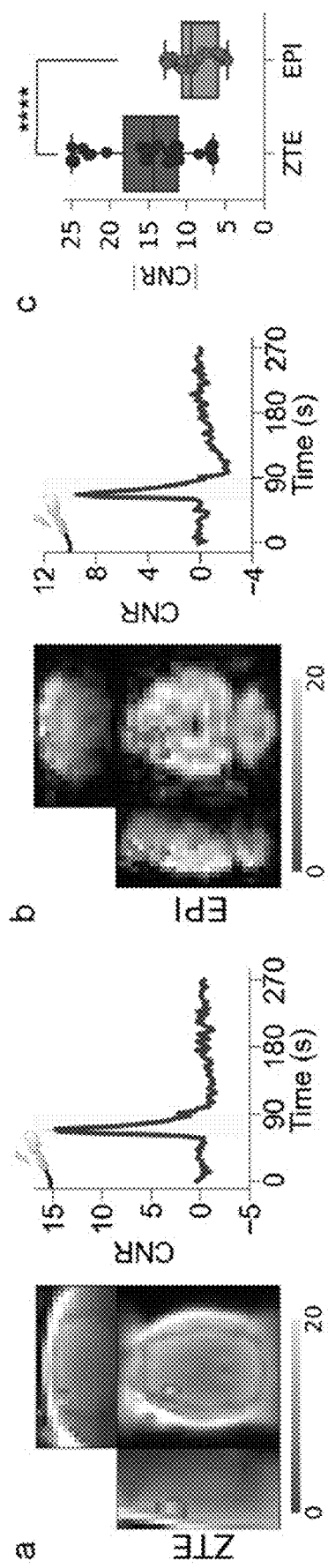
FIG. 6 compares the sensitivity of ZTE and GE-EPI to functional activations is well-established rat-forepaw stimulation paradigm.

Detailed Description of System (1) Optimization of ZTE Imaging parameters for sensitivity to T1-changes. ZTE imaging parameters, flip angle and repetition time (TR) can be modified to specifically target T1 changes following neuronal functional activation. Maximum functional contrast can be calculated for any given baseline T1 value and T1 change through Bloch equation modeling of the steady-state magnetization. FIG. 4A shows the achievable functional contrast efficiency for various TRs and flip angles for a 2% T1 change during functional activation from a physiological baseline of 1,950 ms, a typical gray-matter T1 value at 9.4T in the rodent brain. Complete spoiling of transverse magnetization was assumed as RF spoiling is to be implemented, which sufficiently reduces coherence of residual MR signal. For example, the MRI signal intensity, assuming complete spoiling, can be calculated according to the spoiled gradient recalled echo equation:

$$[H] \frac{Sin(\theta) * \left(1 - e^{\frac{-TR}{T1}}\right)}{1 - \left(Cos(\theta) * e^{\frac{-TR}{T1}}\right)} e^{\frac{-TE}{T2*}},$$

where [H] is the proton density, θ is the flip angle, TR is the repetition time, TE is the echo time, T1 is the T1 relaxation rate and T2* is the T2° relaxation rate. The maximum contrast to T1-related changes can then be calculated as the combination of imaging parameters that gives rise to the greatest difference in MRI signal intensity following a change in the T1 value. This calculation can be modified to take into account different variables, such as incomplete spoiling. TR: For ZTE-fMRI, longer TRs, are favored to reduce the acquisition bandwidth and increase SNR. The modeled contrast was divided by an efficiency term, square root of TR, as a shorter TR allows more spokes to be sampled per unit time which improves the signal-to-noise. The modeled contrast was multiplied by the square root of the readout duration, as longer readout durations reduce the noise variance in each sample. Larger TRs have higher contrast as larger TRs allow for lower acquisition bandwidths. Flip angle: Flip angles on the order of 3° to 6° are favored for maximum sensitivity to T1 changes, thus the low flip angle limitation of hard-pulse ZTE does not diminish its feasibility for fMRI. FIG. 4B shows that the contrast of ZTE-fMRI can be Increased at lower physiological baseline T1 values. As T1 decreases with decreasing field strength, this indicates that ZTE-fMRI contrast may potentially be potentially more robust than EPI at lower magnetic field strengths and by utilizing techniques that shorten baseline T1 values. FIG. 4C demonstrates the relationship between T1 change and maximum contrast, within the range of realistic ZTE-fMRI imaging parameters. Importantly, as the relationship between $PtO_2$ and T1-relaxation rate (R1) is linear, this indicates that the steady-state ZTE signal has the potential to scalably map oxygen-Induced T1 changes. FIG. 4D demonstrates that the contrast of ZTE-fMRI T is minimally affected by the T2* of the brain tissue voxel. This indicates that the source of ZTE-fMRI signal is mostly from T1 changes, and not the blood oxygen level dependent effect. This is corroborated by FIG. 5, which displays the estimated relative contributions of functionally induced cerebral blood flow (CBF), and cerebral blood volume (CBV), and that of $PtO_2$ in the rodent brain following somatosensory stimulation with head-only excitation. Utilizing literature values, inflow-related CBF and CBV contrast was estimated assuming 10 mm/s baseline blood flow in the arterial vasculature and acceleration of 1.5 mm/s over a 1 mm radius, a 20% increase in CBV, while considering the T1 values of the composition of a voxel; blood and tissue, and their relative voxel fractions. Acquisition bandwidth: ZTE MRI data are typically acquired with high acquisition bandwidths to minimize the acquisition delay, to minimize sensitivity to magnetic field inhomogeneity-induced artifacts, and to Increase sensitivity to short T2* species, however a tradeoff of a higher acquisition bandwidth is lower SNR. Because imaging short T2* species Is not necessary for the proposed fMRI applications, the ZTE acquisition bandwidth is minimized to maximize the sensitivity of the technique. FIG. 6 compares the sensitivity of ZTE and GE-EPI to functional activations is well-established rat-forepaw stimulation paradigm. The figure demonstrates that following Bloch equation modeling, to establish optimal imaging parameters, ZTE has superior sensitivity than GE-EPI.

Figures 3A, 3B:
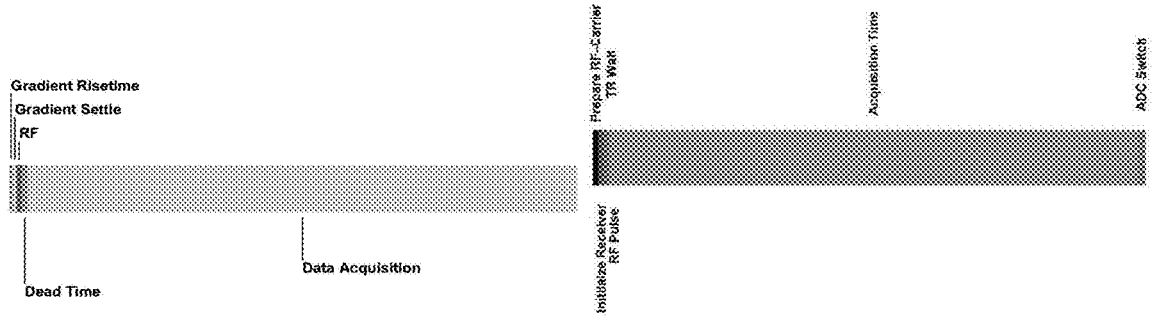
FIGS. 3A-3B illustrate the timing of modules from an example sequence.

(2) Reduction of gradient ramp times. The ramp times of the ZTE spatial encoding gradients at the beginning of image acquisition and between every successive spoke of k-space are minimized based on imaging parameters (field of view, matrix size), hardware limitations (gradient slew rate) and gradient trajectory rather than being set to a constant value. A longer gradient ramp time can be given only at the beginning of acquisition and dummy scans can be set for the MRI signal to reach a steady-state before data acquisition. The gradient ramp delay (gradient rise time in FIG. 3A) is taken to be the incrementation of gradient amplitude divided by slew rate, which ensures gradient has reached plateau, as well as an additional delay (gradient settling time in FIG. 3A) to ensure gradient Eddy currents have stabilized.

(3) Ramping spatial encoding gradients during acquisition. The gradient ramp time and Eddy current settling delays can be removed from the sequence (FIG. 36), by ramping the gradient throughout the acquisition.

(4) RF spoiling. A consequence of maximizing the acquisition efficiency and sensitivity of ZTE is that there is not sufficient time within the radial spoke acquisition duration to implement gradient-spoiling. Therefore, the system can incorporate RF spoiling wherein the phase of the RF-pulse is varied from spoke to spoke, which minimizes residual transverse magnetization, limits formation of spurious echoes and thus improves image SNR and sensitivity to functional activation.

(5) Flexible choice of number of radial spokes. Conventionally the number of radial spokes acquired is defined by the number of spokes required to meet Nyquist's criterion based on the reconstructed matrix size and an undersampling factor. The system can incorporate a flexible choice of the number of acquired radial spokes, independent of image matrix size. This allows better control of sequence temporal resolution and allows for the acquisition of a larger number of spokes for smaller matrix sizes.

Figure 7:
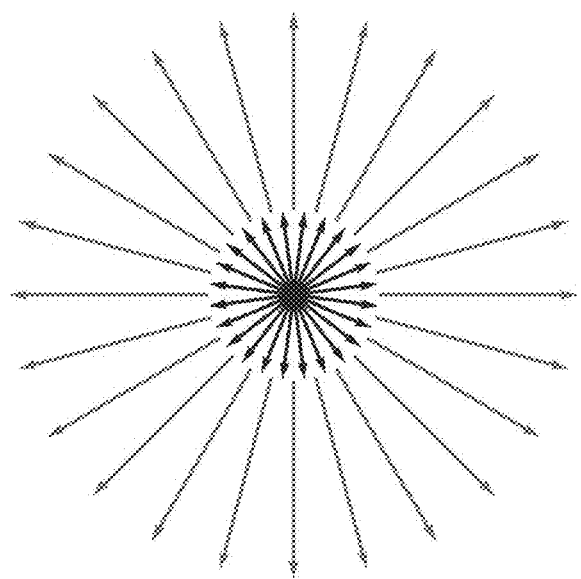
FIG. 7 illustrates an integration of an inner shell with short radial spokes and an outer shell with long radial spokes to provide better sampling in k-space center and periphery.

(6) Dual shell gradient trajectory. As shown in FIG. 7, an integration of an inner shell with short radial spokes and an outer shell with long radial spokes is designed to provide better sampling in k-space center and periphery. The gradient strength required to acquire each shell is determined by the shell size. The two shells are determined to maximize functional contrast and minimize spatial blurring effect. The two shells have a small overlap to ensure the consistency of signal intensity along the radial direction. The dual shell acquisition scheme allows the acquisition of higher spatial-resolution images without sacrificing image quality.

Figure 8:
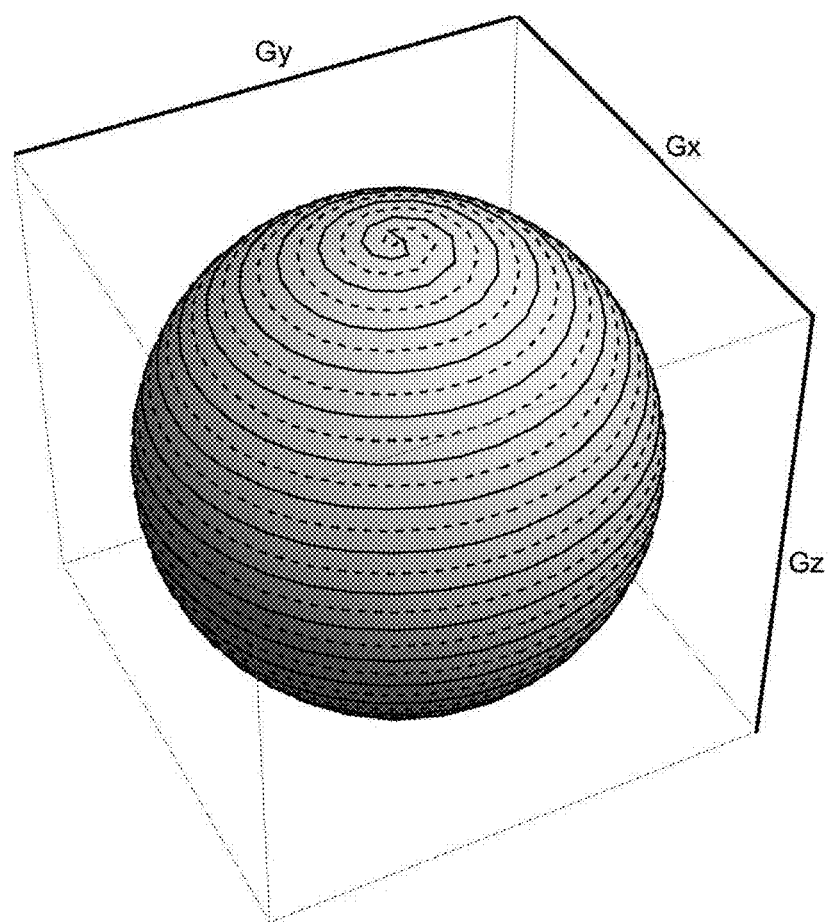
FIG. 8 shows two inverse spiral gradient trajectories to achieve balanced k-space sampling and flexible temporal resolution.

(7) Dual spiral gradient trajectory. As shown in FIG. 8, two inverse spiral gradient trajectories are designed to achieve balanced k-space sampling and flexible temporal resolution. Specifically, the first spiral gradient trajectory starts from the negative z-axis and ends in the positive z axis. While the second spiral starts from the positive z-axis and ends at the negative z-axis. The two spiral trajectories have no overlap in the k-space, allowing compensative sampling, gradient correction, and counterbalancing of motion artifacts. When data from the two trajectories are combined in image reconstruction, a conventional ZTE image is obtained. To improve temporal resolution, the two spiral trajectories are treated as separate acquisitions and reconstructed separately to improve fMRI temporal resolution.

Figure 9:
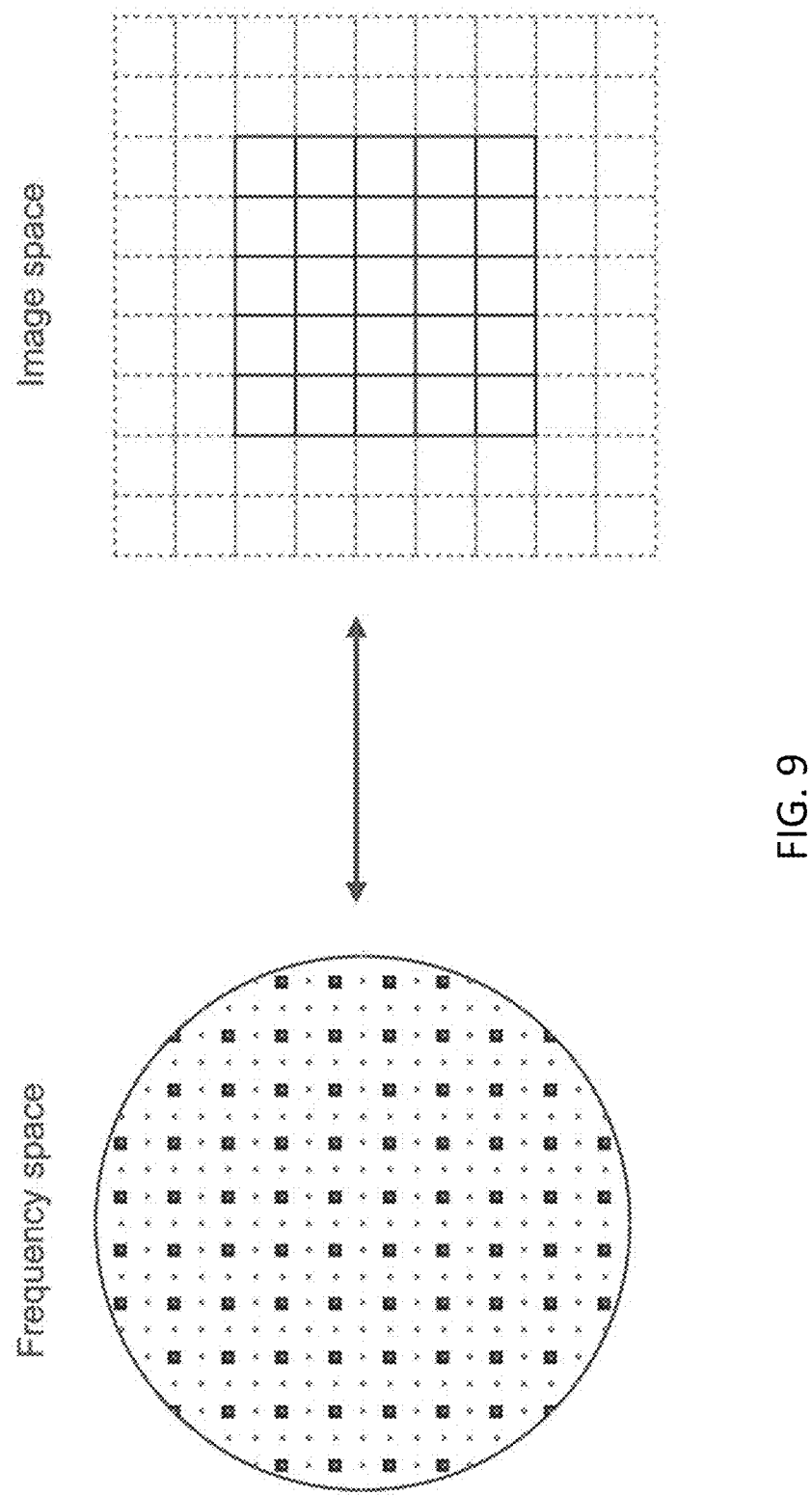
FIG. 9 illustrates a FOV extension in frequency space and image space.
Figure 10:
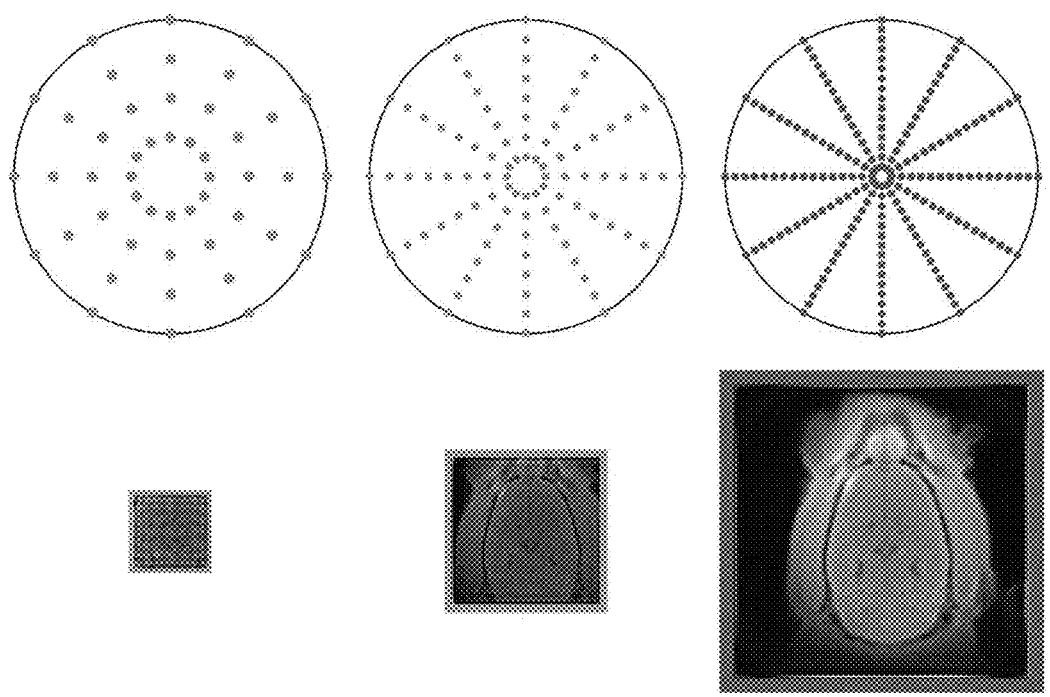
FIG. 10 shows that the oversampled data along the spoke direction can be utilized to extend the original FOV by three extending factors along the x, y and z axes.

(8) Field of view (FOV) extension by data oversampling. FOV extension is used to achieve antialiasing and smaller acquisition bandwidth and improve SNR. FIG. 9 illustrates a FOV extension in frequency space and image space. As shown in FIG. 10, the oversampled data along the spoke direction is utilized to extend the original FOV by three extending factors along the x, y and z axes. The three extending factors are defined as $<\beta_1\ \beta_2,\ \beta_3>$, where each factor is a real number within $$\left[1, \frac{OverSampling}{2}\right].$$

The reconstructed image with extended F V is derived by $$image\ (x, y, z) = \left(\frac{1}{2\pi}\right)^3 *$$

$$\sum_{n_1=-\beta_1*m_1}^{\beta_1*m_1} \sum_{n_2=-\beta_2*m_2}^{\beta_2*m_2} \sum_{n_3=-\beta_3*m_3}^{\beta_3*m_3} f\left(\frac{n_1}{\beta_1}, \frac{n_2}{\beta_2}, \frac{n_3}{\beta_3}\right) * e^{in_1*x+in_2*y+in_3*z}.$$

This capability is crucial because it allows any RF coil to be utilized with the MRI system. It also allows the initial FOV and matrix size to be smaller than the imaging object, allowing further reduction of the acquisition bandwidth, resulting in augmented sensitivity.

Figure 12:
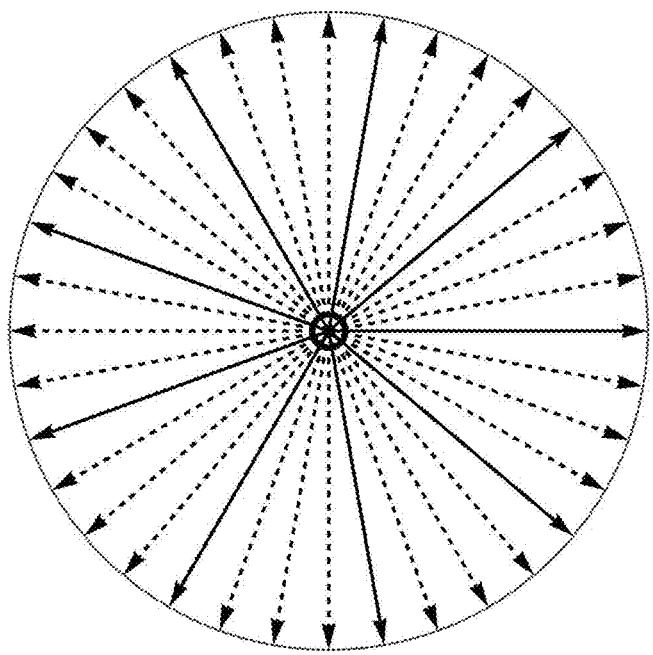
FIG. 12 illustrates radial upsampling, wherein a larger number of spokes are generated via natural interpolation to suppress blurring artifacts

(9) Radial upsampling. To suppress blurring effects due to a limited number of spokes. Raw data is interpolated into a larger number of spokes, as shown in FIG. 12. First, a complete gradient direction is computed based on the minimum spherical k-space sampling required to avoid aliasing. Secondly, a complete gradient trajectory is constructed by multiplying the complete gradient direction and a radial distance vector used to sample the k-space. Third, natural interpolation is used to resample the raw data in the new complete trajectory.

Why is it critical to develop a new fMRI sampling technology for rodents? GRE-based EPI has been the gold standard fMRI technique for nearly three decades due to its ability to rapidly acquire whole brain volumes with MR T2* sensitivity to blood oxygenation—a well-known surrogate marker for brain activity. A recent PubMed search identified ~4,000 new MRI publications per year over the past 10 years. This immensely utilized technique, however, has several drawbacks: (1) high acoustic noise; (2) ghosting and motion artifacts; (3) magnetic field inhomogeneity-related artifacts; (4) low sensitivity compared to other neuroimaging modalities; and (5) poor spatial specificity. A new fMRI sampling technique that addresses these problems has the potential to change day-to-day fMRI practices. In particular, such a development would be of great benefit to the emerging rodent fMRI community because (a) rodents do not tolerate GRE-EPI acoustic noise, leading to many rodent fMRI studies being performed under anesthesia which compromises brain function; (b) awake rodent fMRI studies, albeit possible, suffer from stress and motion confounds unless lengthy habituation protocols are included; (c) most rodent fMRI studies are performed under high magnetic field strengths (>7T), wherein susceptibility artifacts in GRE-EPI are exacerbated.

Why could ZTE serve as an ideal solution and what does it measure? Aptly, imaging sequences with "zero" acquisition delay and minimal increment of gradients are insensitive to problems (1)-(3) above. The benefits of such sequences for fMRI have yet to be documented in humans, although several rodent studies have pointed to the possibility. Nevertheless, these sequences suffer from challenges such as unclear fMRI capability/contrast mechanism, aliasing artifacts, and long acquisition times. It should be noted that none of the short-acquisition-delay sequences have achieved superior sensitivity compared to the gold-standard, GRE-based EPI. These limitations have dampened potential users' enthusiasm and have thus hindered their utilization in functional brain mapping. This document describes systems and methods to overcome these barriers.

In ZTE, each center-out "spoke" measures the immediate free-induction-decay (FID) signal induced by an RF pulse instead of relying on a subsequently generated "echo" with a lengthy T2* decay. The images are formed by reconstructing numerous radially oriented spokes acquired in a 3D frequency domain (i.e., k-space). Owing to its consequently short acquisition delay (several μs), ZTE is insensitive to T2*-weighted BOLD contrast.

We recently conducted various modeling scenarios to explore a range of possible ZTE parameters that can yield robust contrast to T1 changes. We built upon these models and considered the effect of the following ZTE signal modulators in the mouse brain at 9.4T: inflow-related changes in CBF and CBV, and changes to $PtO_2$. The inflow effect in fMRI is attributed to the apparent T1 shortening from inflowing spins that are tagged by few or no RF pulses, which produces a stronger signal than that from saturated stationary tissue.

In ZTE (with head-only RF excitation), frequent RF pulsing will rapidly lead all stationary spins to a steady-state (FIG. 5A, dark dashed line), but the inflowing blood would be subjected to fewer RF pulses and thus would have higher signal than static tissue (FIG. 5A, solid line). Importantly, the voxel signal would also reach a stable steady-state (FIGS. 5B-5C, solid lines), thus changes can be measured. We then modeled activation-induced CBF and CBV changes with inflow considered and found that they contributed to an increase in the ZTE-fMRI signal (FIG. 5B).

Next, we assessed the impact of an increase in $PtO_2$. Guided by Invasive $PtO_2$ measurements and seminal studies identifying the linear relationship between molecular oxygen concentration and T1-relaxation rate (R1), we estimated that the relative contribution of $PtO_2$ changes to the ZTE-fMRI contrast (Figure SC) is at a similar magnitude to that of CBV and CBF contrast combined. Together, these contrast sources give a measurable ZTE-fMRI signal (see FIG. 6). Given that $PtO_2$, CBV and CBF metrics have been shown to exhibit high spatial-specificity in the literature, ZTE-fMRI has the potential to serve as a highly competitive alternative to GRE-EPI. Additionally, as ZTE-fMRI contrast is linear across T1 values in the mouse brain at 9.4T (FIG. 5D), this method has the potential to linearly map brain activity across a range of possible in vivo T1 changes.

Figure 13F:
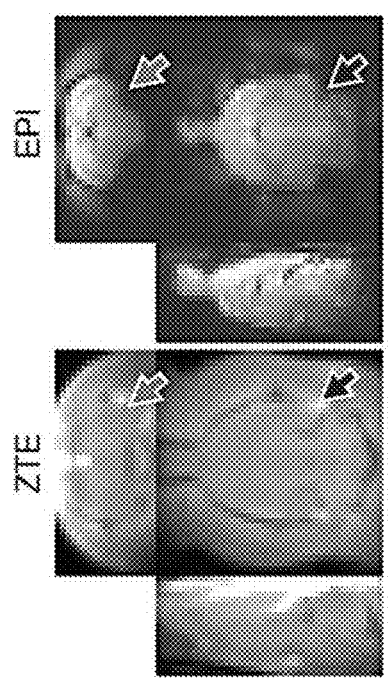

The ZTE method Improvement described herein can achieve contrast-agent-free ZTE-fMRI. We produced a ZTE pulse sequence tailored specifically for fMRI. This sequence provides robust T1 sensitivity (FIG. 13A), superior temporal contrast-to-noise ratio (tCNR) (FIG. 13B), and negligible acoustic noise (FIG. 13C). This sequence also shows tremendous promise for imaging awake mice, as our data reveal a reduction in blood cortisol levels indicative of stress (FIG. 13D), motion parameters (FIG. 13E), and susceptibility artifacts (FIG. 13F) as compared to GRE-EPI. Importantly, we obtained evidence in rats showing the superior sensitivity of ZTE-fMRI compared to GRE-EPI at 9.4T (FIG. 6).

How is ZTE different from other contrast-agent-free fMRI alternatives?

To-date, no fMRI sampling strategy can be used to address five major limitations of the most widely used GRE-EPI-fMRI technique:

1) High acoustic noise. MRI scanning is often associated with intense acoustic noise, as gradient coils vibrate loudly when driven by rapidly switching electrical currents. EPI generates particularly severe acoustic noise due to the high gradient-power duty cycle of the sequence and the need to invert gradient polarity during spatial encoding. This prevents imaging animals in the awake condition unless the subject undergoes a lengthy training/habituation procedure. Even with successful habituation in resting-state fMRI studies, the brain's auditory system is, presumably, in a different state while intense noise is being heard.

Figure 11:
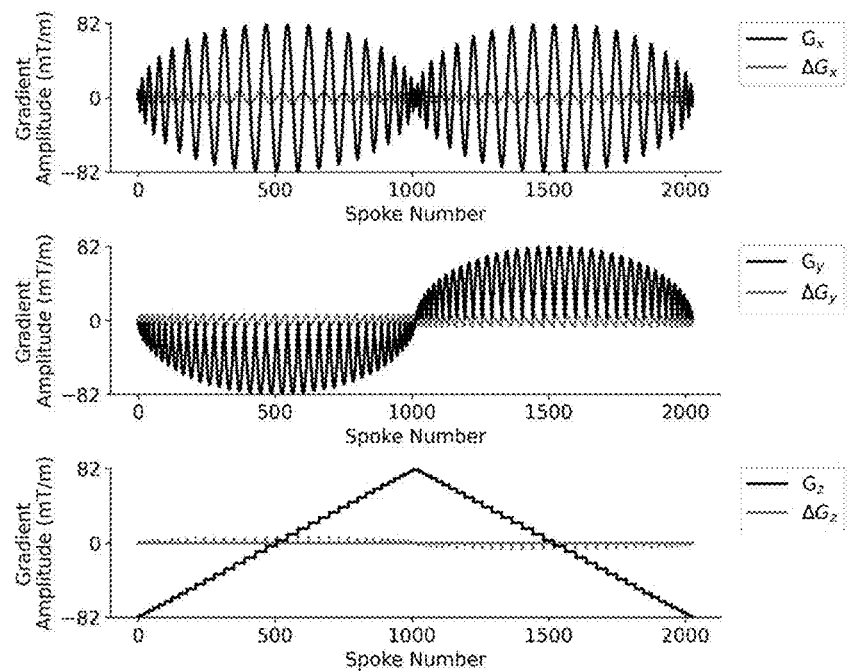
FIG. 11 shows the ZTE encoding gradient amplitude during acquisition and step change between spokes.

ZTE-fMRI is silent because rapid switching of gradient polarity is not required. During the acquisition of a ZTE spoke, no acoustic noise would be generated because the gradient amplitude stays constant. Between any two successive spoke acquisitions, we use a trajectory designed to yield minimal gradient directional changes which result in negligible acoustic noise. We will utilize a trajectory design where the last gradient direction at the end of the acquisition volume aligns with the beginning of the next volume to circumvent the need to reset the gradient between volumes, which will further minimize acoustic noise. Faster slew rates induce more significant acoustic noise due to faster oscillation of Lorentz forces within the gradient coils. FIG. 11 displays the encoding gradient amplitude during acquisition and maximum encoding gradient amplitude step between spokes for the conventional ZTE sequence as shown in FIG. 2A. In this example the maximum slew rate is 0.032 T/m/s. Due to the longer acquisition duration afforded by removing the gradient ramp time and Eddy current settling times, the maximum slew rate of the ramp-sampling ZTE sequence as shown in FIG. 2B is 0.00158 T/m/s. For comparison, the maximum slew rate of an EPI sequence with equivalent imaging parameters would be 59.4 T/m/s.

2) Ghosting and motion artifacts. In conventional EPI, every other k-space line is acquired in the opposite direction. Ghosting artifacts result from phase errors introduced when echoes formed by these forward and backward k-space encodings exhibit a temporal mismatch. Eddy currents from coils and the magnet housing during EPI induce phase shifts. Additionally, physical motion contributes to ghosting, often as a result of the "blipped" spatial encoding gradient incrementation and relatively low bandwidth in the phase encoding direction. It is well-established that datapoints closer to the center of the k-space encode critical information about bulk object location and contrast. As EPI equally samples the k-space, any transient motion during low-frequency k-space sampling would be represented as bulk motion following reconstruction.

ZTE-fMRI is highly resistant to ghosting and motion artifacts because conventional phase-encoding is absent and the bandwidth is uniform across k-space. ZTE uses a 3D radial "koosh-ball" sampling scheme which densely encodes information around the k-space center, thereby distributing the energy of transient motion into thousands of encoding directions, resulting in a more honest reflection of the object location during a volume TR. PROPELLER or other center-out encoding schemes such as Spiral EPI have shown great promise in reducing ghosting and motion artifacts. Our ZTE sequence will inherit these artifact-resisting properties.

3) Susceptibility artifacts and distortion. Non-uniform magnetic fields generate image distortion and signal loss, often referred to as susceptibility artifacts. Such artifacts commonly exist in GRE-EPI-fMRI because strong BOLD contrast occurs at a long echo time (TE) on the order of tens of ms. Using a long TE inevitably generates significant T2* dephasing of brain tissue signal. In animals, susceptibility artifacts appear in several key brain regions around the inner ear, including the amygdala. Conventionally, this could be partially mitigated by injecting aprotic materials such as fomblin or toothpaste into the inner ear which is not trivial in day-to-day practice. Eddy-current-induced field inhomogeneity and low phase-encoding bandwidth in GRE-EPI also induce significant distortion.

ZTE-fMRI is immune to susceptibility artifacts and distortion because it encodes data immediately after RF excitation, leaving essentially no time for significant voxel dephasing. Also, as all datapoints are sampled using frequency encoding within a short readout time (<0.5-1.0 ms), the phase deviation from encoding is minimized. This also renders the ZTE-fMRI sequence Insensitive to geometric distortion. This feature facilitates studies of brain regions susceptible to field inhomogeneity and simplifies motion correction to rigid-body registration.

4) Low sensitivity compared to other non-fMRI modalities. While GRE-EPI-fMRI is considered the most robust conventional fMRI technique, it has lower sensitivity than alternative functional imaging modalities. A wealth of literature has documented the benefits of sensitivity gain in improving fMRI spatiotemporal resolution, which allows finer activity changes to be mapped. Achieving higher fMRI sensitivity has proven to be challenging and remains of great interest to MR scientists. Sensitivity gain will benefit brain researchers using animal models and ensure that fMRI remains a pivotal technology for translational brain science.

ZTE-fMRI is sensitive because we will strategically select TR, FA, and minimize the required encoding preparation. Conventionally, EPI necessitates a high acquisition bandwidth to rapidly encode the entirety of k-space between every RF pulse repetition. In contrast, our proposed ZTE-fMRI technique utilizes a low acquisition bandwidth ($\leq$50 kHz) to acquire data with high SNR. We have demonstrated robust ZTE-fMRI SNR at little to no penalty to magnetic field inhomogeneity-related artifacts, and the system can improve SNR further (see FIG. 6). In addition, we also propose a low-risk, high-reward strategy to boost sensitivity by using an established MEMRI strategy to shorten tissue T1. Because ZTE-fMRI changes are greater at shorter baseline T1, this grants ME-ZTE-fMRI a sensitivity boost and makes it a compelling technology to image awake mouse brain function without undue stress confounds.

5) Poor spatial specificity. The BOLD contrast utilized by GRE-EPI-fMRI studies is weighted towards venous vasculature. Techniques more localized to arterioles and capillaries are suggested to be more spatially specific because their changes are closer to neuronal activation. The interpretation of GRE-EPI-fMRI data is hindered by its spatial non-specificity and requires anatomical knowledge of the underlying vasculature locations.

ZTE is specific because it is sensitive to CBF, CBV, and $PtO_2$ changes (see FIG. 5). CBF and CBV are proven to be more spatially specific than BOLD. Further, oxygen is predominantly released at capillaries and arterioles, in closer proximity to the source of neuronal activity. Thus, ZTE's sensitivity to CBF, CBV, and $PtO_2$ changes grants improved spatial specificity with respect to functional activation versus GRE-EPI.

Ramp-Sampling ZTE

FIG. 2B shows a timing diagram for a Ramp-Sampling ZTE sequence. In Ramp-Sampling ZTE:

1. Data will be acquired during gradient modulation.
2. Curved sampling of k-space, resulting in improved sampling density in high frequency domain, benefitting parallel imaging and high resolution imaging.
3. Minimum gradient slew rate requirement and smallest acoustic noise.
4. Reduced interference on electrophysiological recording.
5. Broader and easier sequence dissemination.

Curved Sampling of k-Space

Gradient performs linear change during data acquisition $$G = G_0 + \Delta G$$

Spoke curve is defined as the $$p(x, y, z, t) = \int_0^t G_x(t)dt + \int_0^t G_y(t)dt + \int_0^t G_z(t)dt =$$
$$G_0 \times t + \frac{1}{2}\Delta G_x \times t^2 + \frac{1}{2}\Delta G_y \times t^2 + \frac{1}{2}\Delta G_z \times t^2, t \in [0, 1]$$

Considering of some delay time $\Delta d$ $$p(x, y, z, t) = G_0 \times (t - \Delta d) + \frac{1}{2}(\Delta G_x + \Delta G_y + \Delta G_z) \times (t - \Delta d)^2$$

Let t=1, the spoke length is constant:

$$\|G_0 + (\Delta G_x + \Delta G_y \Delta G_z)\|^2 = R^2$$

The curved spoke cannot reach to the k-max, because $$\|p(x, y, z, 1)\|^2 \leq G_{0x}^2 + G_{0y}^2 + G_{0z}^2 + \frac{1}{4}(\Delta G_x^2 + \Delta G_y^2 + \Delta G_z^2) \leq R^2$$

Where $\Delta d$ is mainly determined by the angular undersampling.

Figure 14:
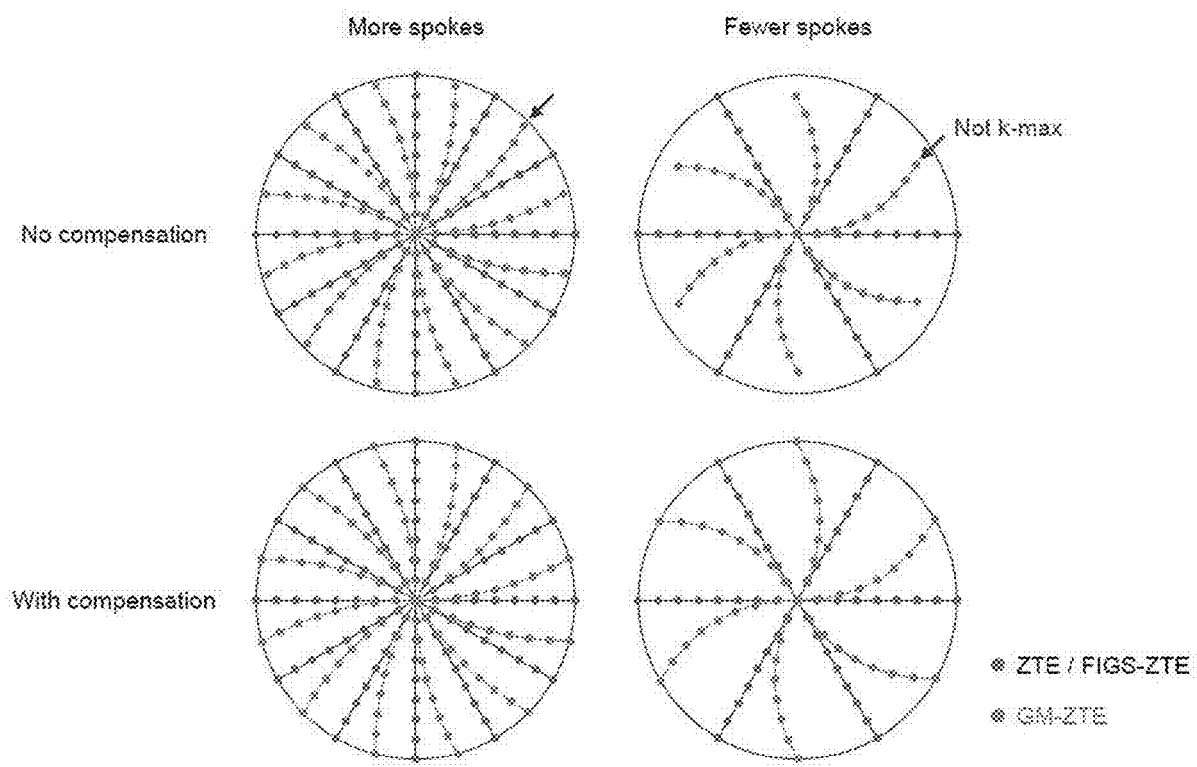
FIG. 14 illustrates compensation of the curved spoke.

FIG. 14 illustrates compensation of the curved spoke. The curved spokes are shown both with no compensation and with compensation.

Although specific examples and features have been described above, these examples and features are not intended to limit the scope of the present disclosure, even where only a single example is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed in this specification (either explicitly or implicitly), or any generalization of features disclosed, whether such features or generalizations mitigate any or all the problems described in this specification. Accordingly, new claims may be formulated during prosecution of this application (or an application claiming priority to this application) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A system for functional magnetic resonance imaging, the system comprising:
   a magnetic resonance imaging (MRI) scanner; and
   a control console implemented on at least one processor and configured for:
      executing, using the MRI scanner, a zero echo time (ZTE) pulse sequence;
      acquiring, using the MRI scanner, magnetic resonance data in response to the ZTE pulse sequence; and
      constructing at least one MRI image using the magnetic resonance data and measuring tissue oxygenation ($PtO_2$)-related T1 changes as a proxy of neural activity changes of a subject using the at least one MRI image.

2. The system of claim 1, wherein executing the ZTE pulse sequence comprises applying a spatially non-selective radio frequency pulse after one or more spatial encoding gradients have reached a plateau, and wherein executing the ZTE pulse sequence comprises setting a delay before the application of subsequent radio frequency pulses, wherein the delay is based on a gradient ramp time and a settling time for Eddy currents.

3. The system of claim 1, wherein executing the ZTE pulse sequence comprises adjusting one or more ZTE imaging parameters for sensitivity to $PtO_2$-related T1 changes.

4. The system of claim 3, wherein adjusting one or more ZTE imaging parameters for sensitivity to $PtO_2$-related T1 changes comprises modifying TR and flip angle to target $PtO_2$-related T1 changes following neuronal functional activation/deactivation.

5. The system of claim 3, wherein adjusting one or more ZTE imaging parameters for sensitivity to $PtO_2$-related T1 changes comprises optimizing imaging parameters through Bloch equation simulations.

6. The system of claim 1, wherein executing the ZTE pulse sequence comprises minimizing ZTE acquisition bandwidth to augment sensitivity, or increasing bandwidth to reduce artifacts including magnetic field inhomogeneity-related artifacts.

7. The system of claim 1, wherein executing the ZTE pulse sequence comprises minimizing the ramp time of a ZTE spatial encoding gradient at a beginning of image acquisition and between each successive spokes of k-space.

8. The system of claim 1, wherein executing the ZTE pulse sequence comprises incorporating RF-spoiling wherein the phase of a RF pulse is varied from each spoke of a plurality of spokes.

9. The system of claim 1, wherein executing the ZTE pulse sequence comprises integrating an inner shell with short radial spokes and an outer shell with long radial spokes.

10. The system of claim 1, wherein executing the ZTE pulse sequence comprises using two inverse spiral gradient trajectories.

11. A method for functional magnetic resonance imaging, the method comprising:
   executing, using an MRI scanner, a zero echo time (ZTE) pulse sequence, wherein executing the ZTE pulse sequence comprises applying a spatially non-selective radio frequency pulse after one or more spatial encoding gradients have reached a plateau, and wherein executing the ZTE pulse sequence comprises setting a delay before the application of subsequent radio frequency pulses, wherein the delay is based on a gradient ramp time and a settling time for Eddy currents;
   acquiring, using the MRI scanner, magnetic resonance data in response to the ZTE pulse sequence; and
   constructing, at a control console implemented on at least one processor, at least one MRI image using the magnetic resonance data and measuring neural activity of a subject using the at least one MRI image.

12. The method of claim 11, wherein executing the ZTE pulse sequence comprises adjusting one or more ZTE imaging parameters for sensitivity to $PtO_2$-related T1 changes.

13. The method of claim 12, wherein adjusting one or more ZTE imaging parameters for sensitivity to $PtO_2$-related T1 changes comprises modifying flip angle and repetition time to target T1-related $pO_2$ changes following neuronal functional activation.

14. The method of claim 12, wherein adjusting one or more ZTE imaging parameters for sensitivity to $PtO_2$-related T1 changes comprises optimizing imaging parameters through Bloch equation simulations.

15. The method of claim 11, wherein executing the ZTE pulse sequence comprises minimizing ZTE acquisition bandwidth to augment sensitivity.

16. The method of claim 11, wherein executing the ZTE pulse sequence comprises incorporating RF-spoiling wherein the phase of a RF pulse is varied from each spoke of a plurality of spokes.

17. A method for functional magnetic resonance imaging, the method comprising:
   executing, using an MRI scanner, a zero echo time (ZTE) pulse sequence, wherein executing the ZTE pulse sequence comprises minimizing the ramp time of a ZTE spatial encoding gradient at a beginning of image acquisition and between each successive spokes of k-space;
   acquiring, using the MRI scanner, magnetic resonance data in response to the ZTE pulse sequence; and
   constructing, at a control console implemented on at least one processor, at least one MRI image using the magnetic resonance data and measuring neural activity of a subject using the at least one MRI image.

18. The method of claim 11, wherein executing the ZTE pulse sequence comprises using two inverse spiral gradient trajectories.

19. The method of claim 11, wherein executing the ZTE pulse sequence comprises integrating an inner shell with short radial spokes and an outer shell with long radial spokes.

* * * * *